United States Patent [19]

McKubre et al.

[11] Patent Number: 5,006,786
[45] Date of Patent: Apr. 9, 1991

[54] DEVICE FOR IN SITU MONITORING OF CORROSION RATES OF POLARIZED OR UNPOLARIZED METALS

[75] Inventors: Michael C. H. McKubre, San Mateo County; Barry C. Syrett, Santa Clara County, both of Calif.

[73] Assignee: Electric Power Research Institute, Inc., Palo Alto, Calif.

[21] Appl. No.: 518,256

[22] Filed: May 3, 1990

Related U.S. Application Data

[63] Continuation of Ser. No. 353,189, May 16, 1989, abandoned, which is a continuation of Ser. No. 38,164, Apr. 14, 1987, abandoned, which is a continuation-in-part of Ser. No. 576,119, Feb. 2, 1984, Pat. No. 4,658,365.

[51] Int. Cl.$^5$ .......................................... G01N 27/26
[52] U.S. Cl. ................................ 324/71.2; 324/71.1; 204/153.11
[58] Field of Search .............. 324/71.1, 71.2, 425, 324/557; 204/404, 1 C, 1 T, 153.11, 153.1; 364/496

[56] References Cited

U.S. PATENT DOCUMENTS

| | | | |
|---|---|---|---|
| 3,878,064 | 4/1975 | Weisstuch et al. | 204/404 X |
| 4,056,445 | 11/1977 | Gauntt et al. | 204/404 X |
| 4,099,117 | 7/1978 | Erath | 324/557 |
| 4,238,298 | 12/1980 | Tsuru et al. | 204/1 C |
| 4,658,365 | 4/1987 | Syrett et al. | 364/496 |

Primary Examiner—Kenneth Wieder
Assistant Examiner—Jack B. Harvey
Attorney, Agent, or Firm—Flehr, Hohbach, Test, Albritton & Herbert

[57] ABSTRACT

A technique for electrochemical measurement of the corrosion current (corrosion rate) determines the electrochemical parameters that are necessary to calculate the corrosion rate as they are contained in the harmonic current response to a moderate amplitude sinusoidal voltage perturbation applied to the corroding metallic component. The harmonic current response is analyzed at frequencies $1f$, $2f$, $3f$, $4f$, $5f$ and the rectification current response of DC current to the presence of a 20–50 mV AC voltage perturbation at a frequency f. The free corrosion current density, the free corrosion potential and the Tafel coefficients are calculated. The Tafel coefficient or Tafel slope is a measure of the exponential dependence at the rate of corrosion in a material. From these data, the dissolution current is calculated, which in turn is integrated with respect to time to yield a cumulative mass loss.

8 Claims, 8 Drawing Sheets

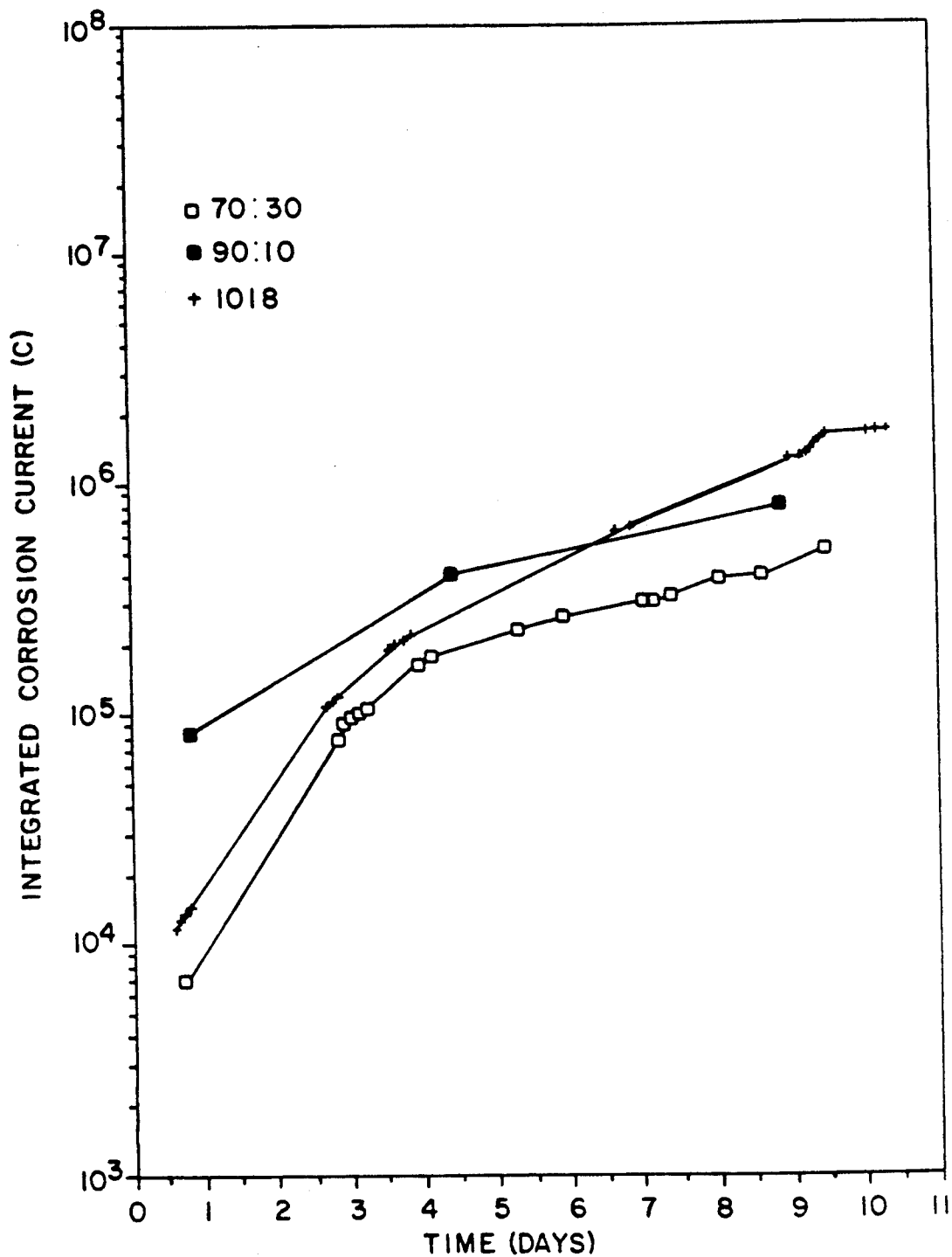
FIG. — 10

DEVICE FOR IN SITU MONITORING OF CORROSION RATES OF POLARIZED OR UNPOLARIZED METALS

CROSS REFERENCE TO RELATED APPLICATION

This is a continuation of application Ser. No. 353,189 filed on May 16, 1989, now abandoned, which is a continuation of application Ser. No. 038,164 filed on Apr. 14, 1987, now abandoned, which is a continuation-in-part of Ser. No. 516,119, filed Feb. 2, 1984, now U.S. Pat. No. 4,658,365, issued 4/14/87.

BACKGROUND OF THE INVENTION

This invention is directed generally to methods of measuring corrosion rate in metals. The above-referenced application described measurement of the corrosion rates of cathodically protected systems. In this application, methods are described for extending this analysis to calculation of corrosion rates at any applied potential (cathodic or anodic) or at the free corrosion potential.

In situ electrochemical techniques have already been applied successfully in measuring corrosion rates of freely corroding metals. Analysis of the response of an electrode to small amplitude ($<10$ mV) sinusoidal voltage perturbations forms the basis of the well established technique known as AC impedance spectroscopy. In studies of corrosion, a small amplitude perturbation is imposed about the free corrosion potential, and the impedance ($Z=V/I$, where $\sim$ denotes a complex variable, V is voltage, and I is current) is extrapolated to a real value at low frequency to define a "corrosion resistance," $R_{corr}$, that is characteristic of a particular electrode/electrolyte combination. The Stern-Geary relationship may be used to calculate the corrosion current, $I_{corr}$, as follows:

$$I_{corr} = \beta_a \beta_c / 2.303 \, R_{corr} (\beta_a + \beta_c) \quad (1)$$

where $\beta_a$ and $\beta_c$ are the Tafel coefficients for anodic and cathodic partial reactions, respectively.

The derivation leading to Eq. 1 assumes that the corroding electrode responds linearly to the imposed electrical perturbations; that is, doubling the perturbing voltage amplitude results in a doubled current response (but an unchanged impedance). Since physical variables in all physically realizable systems must have a finite first derivative, it is always possible to achieve linear conditions by applying a perturbation of limitingly small amplitude. The nonlinearity of the current/voltage relationship in corroding systems prohibits the use of conventional AC impedance spectroscopy, either at DC potentials more than a few millivolts from the free corrosion potential or using other than a limitingly small perturbation. The reason is that, in a nonlinear system, the electrical perturbation, which is imposed on the system at a frequency of f, results in a response at $_2f$, $_3f$, $_4f$, etc., in addition to a DC component. Neither the fundamental response ($_of$) nor the total power response $$\left( \sum_{h=0}^{\infty} h^f \right)$$

can be analyzed to determine the corrosion resistance uniquely. The use of Eq. 1 to determine corrosion rates presumes that the term $B = \beta_a \beta_c / (\beta_a + \beta_c)$ is known. In real systems, B may be difficult to determine without large voltage perturbations which may modify the surface of interest. Even if a value of B is determined by a second experiment, this value may vary during the course of an experiment. Values of $R_{corr}$ can thus only be used to give a qualitative indication of the corrosion rate.

A number of fairly common situations exist in which the potential of the metal of interest is much more than a few millivolts from the free corrosion potential; in these situations, the Stern-Geary relationship (Eq. 1) is invalid, as discussed above. For example, the well known corrosion control techniques of cathodic protection and anodic protection typically result in a shift in the potential of the metal by several hundred millivolts from the free corrosion potential. Similarly, large shifts in the potential can result when a metal is galvanically coupled to another dissimilar metal. Thus, a technique for monitoring corrosion rates at any potential without the need for separate measurements of $\beta_a$ and $\beta_c$ would be highly useful and have enormous potential for use.

SUMMARY OF THE INVENTION

It is therefore an object of this invention to provide an electrochemical technique for monitoring the corrosion rate of a structure more accurately and under a much wider range of conditions than can be obtained using existing methods.

Corrosion rate may be determined by making periodic weight loss measurements on the corroding metals. This is a time consuming process and the results are interpretable only if flow conditions and environmental conditions remain constant.

It is therefore an object of this invention to provide an improved, automated method for determining corrosion rate of a metal.

The above and other objectives are achieved by a technique for electrochemical measurement of the corrosion current (corrosion rate). The electrochemical parameters that are necessary to calculate the corrosion rate are contained in the harmonic current response to a moderate amplitude sinusoidal voltage perturbation applied to the corroding metallic component. The harmonic current response is analyzed at frequencies $_1f$, $_2f$, $_3f$, $_4f$, $_5f$ and the rectification current response at DC current to the presence of a 20-50 mV AC voltage perturbation at a frequency f. The free corrosion current density, the free corrosion potential and the Tafel coefficients are calculated. The Tafel coefficient or Tafel slope is a measure of the exponential dependence at the rate of corrosion in a material. From these data, the dissolution current is calculated, which in turn is integrated with respect to time to yield a cumulative mass loss.

It is believed that the method disclosed herein can be a powerful research tool, allowing an investigator to rapidly evaluate the effects of changes in control potential or current, flow conditions, or water chemistry. Application of the results of this technique could further be used for monitoring the corrosion rate of any structure.

BRIEF DESCRIPTION OF THE DRAWINGS

This invention can be best explained with reference to the following figures, wherein:

FIGS. 9 and 10 illustrate the results of the experiments described above.

DETAILED DESCRIPTION OF A PREFERRED EMBODIMENT

Figure 1:
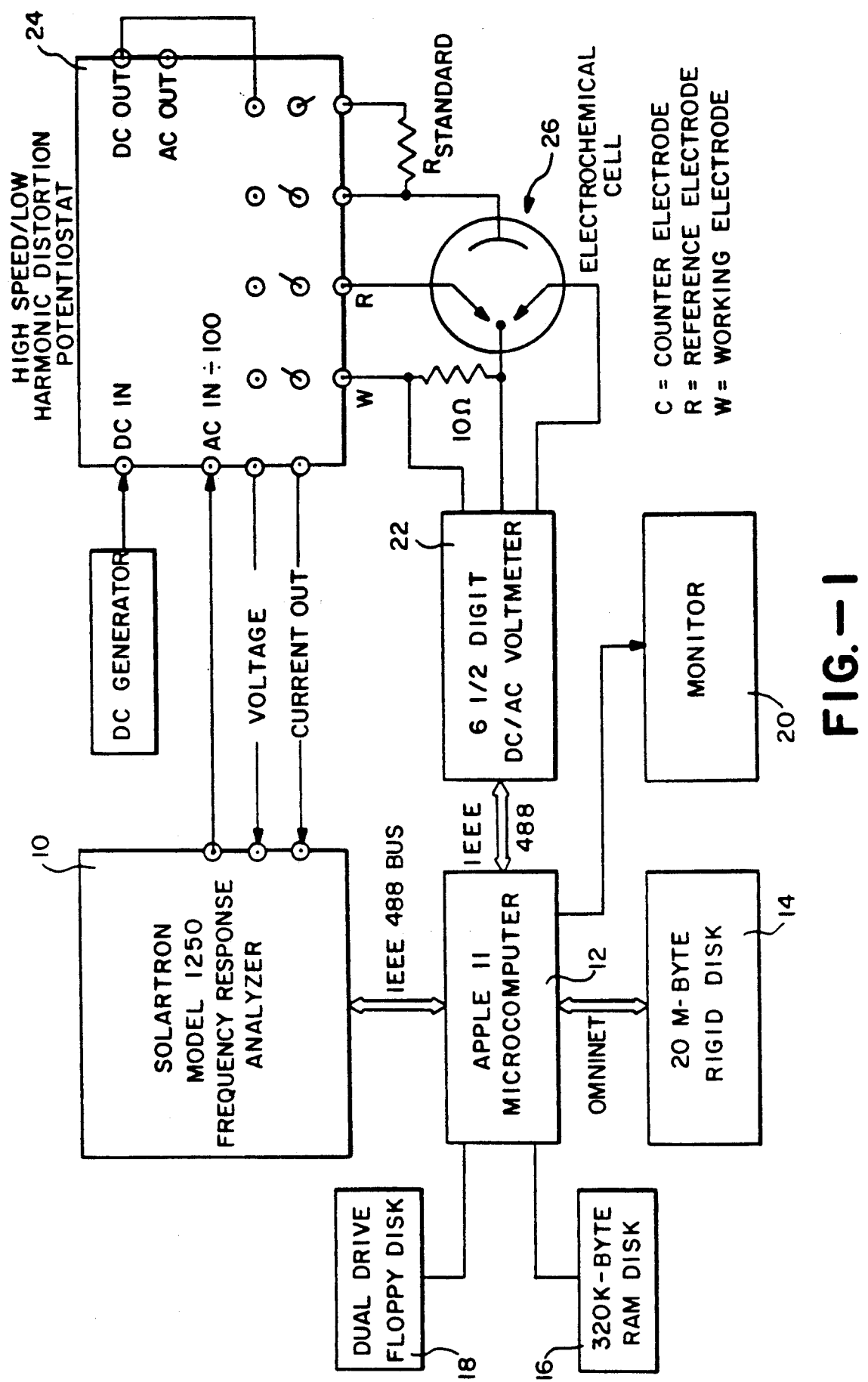
FIG. 1 is a block diagram of the equipment used to develop the necessary parametric information to develop the data of interest.

A simplified theoretical basis for the analysis of harmonic responses to estimate corrosion rates is described below. The necessary measurements are made using the microcomputer controlled equipment of FIG. 1.

Assuming that both the anodic and cathodic corrosion processes can be described by the Butler-Volmer equation, and that the free corrosion potential is sufficiently far from the reversible potentials of the two partial processes, then when the electrode being measured is polarized, the corresponding Faradaic current (the corrosion rate) will be given by $$I = I_{fc}[e^{\beta_a \eta} - e^{-\beta_c \eta}] \quad (2)$$

where $$\eta = V_{applied} - V_{fc} \quad (3)$$

where $I_{fc}$ is the current at the free corrosion potential, $V_{applied}$ is the applied potential, and $V_{fc}$ is the free corrosion potential.

The two exponential terms can be expanded using a Taylor series expansion:

$$\exp(\beta_a \eta) = 1 + \beta_a \eta + \frac{(\beta_a \eta)^2}{2!} + \frac{(\beta_a \eta)^3}{3!} + \ldots \quad (4)$$

$$\exp(-\beta_c \eta) = 1 - \beta_c \eta + \frac{(\beta_c \eta)^2}{2!} - \frac{(\beta_c \eta)^3}{3!} + \ldots \quad (5)$$

hence, $$I = I_{fc}[(\beta_a + \beta_c)\eta + (\beta_a^2 - \beta_c^2)\eta^2/2! + \quad (6)$$

$$(\beta_a^3 + \beta_c^3)\eta^3/3! + \ldots]$$

(a) Measurements at the Free Corrosion Potential

If the electrode is polarized by a sinusoidal perturbation about the free corrosion potential, then $$\eta = v \sin(\omega t) \quad (7)$$

$$\eta^2 = v^2 \sin^2(\omega t) = v^2 \frac{1 - \cos(2\omega t)}{2} \quad (8)$$

-continued $$\eta^3 = v^3 \sin^3(\omega t) = v^3 \frac{3 \sin(\omega t) - \sin(3\omega t)}{4} \quad (9)$$

Substituting Eqs. 7, 8 and 9 into 6 yields the harmonic expression for the Faradaic current:

$$I = I_{fc} \{[(\beta_a + \beta_c)v \sin(\omega t)] + \quad (10)$$

$$\frac{1}{2}(\beta_a^2 - \beta_c^2)v^2 \frac{1 - \cos(2\omega t)}{2} +$$

$$1/6(\beta_a^3 + \beta_c^3)v^3 \frac{3\sin(\omega t) - \sin(3\omega t)}{4} + \ldots \}$$

For small values of v (ignoring powers >3), $$I = I_{fc}\{[\frac{1}{4}(\beta_a^2 - \beta_c^2)v^2] + \quad (11)$$

$$\{(\beta_a + \beta_c)v + \frac{1}{8}(\beta_a^3 + \beta_c^3)v^3\}\sin(\omega t) -$$

$$\frac{1}{4}(\beta_a^2 - \beta_c^2)v^2 \cos(2\omega t) - 1/24(\beta_a^3 + \beta_c^3)v^3 \sin(3\omega t)\}$$

defining the function $$M_n = [\beta_a^n - \beta_c^n(-1)^n]v^n/2^n \quad (12)$$

We can establish a simple matrix for the expected harmonic responses for a purely Faradaic corrosion process perturbed about the free corrosion potential. The values of $_hI/I_{fc}$ are predicted to be as follows:

|   |   | Real Response | | | | Imaginary Response | | |
|---|---|---|---|---|---|---|---|---|
| n = | 0 | 1 | 2 | 3 | | 1 | 2 | 3 |
| No. 0 | 0 | 0 | $M_2$ | 0 | | — | — | — |
| 1 | 0 | $2M_1$ | 0 | $M_3$ | | 0 | 0 | 0 |
| 2 | 0 | 0 | 0 | 0 | | 0 | $-M_2$ | 0 |
| 3 | 0 | 0 | 0 | $-M_3/3$ | | 0 | 0 | 0 |

$_hI/I_{fc}$

From the above matrix, again using presubscripts ($_hI$) to denote the harmonic number, we can predict the response at each harmonic as $$_0I = I_{fc}M_2 \quad (13)$$

$$_1I = 2I_{fc}M_1 \text{ assuming that } M_1 >> M_2 \text{ and } M_3 \quad (14)$$

$$_2I = -I_{fc}M_2 \quad (15)$$

$$_3I = -I_{fc}M_3/3 \quad (16)$$

These represent the fundamental current and first, second and third harmonics.

Solving simultaneously for $I_{fc}$ in Eqs. 13-16, we obtain $$I_{fc} = {_1I}^2/[(48)(_2I_3I - _2I^2)]^{\frac{1}{2}} \quad (17)$$

(the free corrosion current) and $$\beta_c, \beta_a = \frac{_2I \pm [48_3I \cdot _1I - _2I^2]^{\frac{1}{2}}}{_1I} \quad (18)$$

(the anodic and cathodic Tafel coefficients).

Eqs. 17 and 18 are similar in form of those derived by Naixin.

(b) Measurements at Anodic or Cathodic Potentials

Under an applied anodic or cathodic bias.

$$\eta = V + v\sin(\omega t) \qquad (19)$$

Substituting Eq. 19 into Eq. 2, we obtain $$I = I_{fc}[e^{V\beta_a}e^{v\beta_a\sin(\omega t)} - e^{-V\beta_c}e^{-v\beta_c\sin(\omega t)}] \qquad (20)$$

That is, for conditions in which $V \neq 0$, terms in $\beta_a$ must be multiplied by $eV\beta_a$ and terms in $\beta_c$ must be multiplied by $e - V\beta_c$. The matrix following Eq. 12 therefore remains correct, but the function $M_n$ must be modified as follows:

$$M_n' = [(\beta_a e^{V\beta_a})^n - (-\beta_c e^{-V\beta_c})^n]\frac{v^n}{2^n} \qquad (21)$$

The values of $_hI/I_{fc}$ for a purely Faradaic corrosion process sinusoidally perturbed at any potential are therefore predicted to be as follows:

| | | Real Response | | | Imaginary Response | | |
|---|---|---|---|---|---|---|---|
| | | | | | $_h I/I_{fc}$ | | |
| Due to | n = | 0 | 1 | 2 | 3 | 1 | 2 | 3 |
| Harmonic No. | 0 | 0 | 0 | $M_2$ | 0 | — | — | — |
| | 1 | 0 | $2M'_1$ | 0 | $M'_3$ | 0 | 0 | 0 |
| | 2 | 0 | 0 | 0 | 0 | 0 | $-M'_2$ | 0 |
| | 3 | 0 | 0 | 0 | $-M'_3/3$ | 0 | 0 | 0 |

Eq. 21 differs from Eq. 12 in two important ways. First, the extra terms for the general solution given in Eq. 21 contain an additional unknown, V, which must be solved for if the voltage difference between the potential of the structure and the free corrosion potential is unknown. Second, the anodic and cathodic Tafel coefficients are modified, in the general case, by factors that depend exponentially on V (the anodic or cathodic overvoltage). As the level of cathodic bias is increased (V made increasingly more negative), the terms involving $\beta_a$ become less significant. The values of $\beta_a$, $\beta_c$, $I_{fc}$ and V are obtained by the computer best-fit of the measured harmonic current responses to Eqs. 20, 21 and the matrix that follows Eq. 21. These values are then used together with Eqs. 2 and 3 to calculate the corrosion current.

(c) Experimental Methods of Implementing Harmonic Analysis

Figure 2:
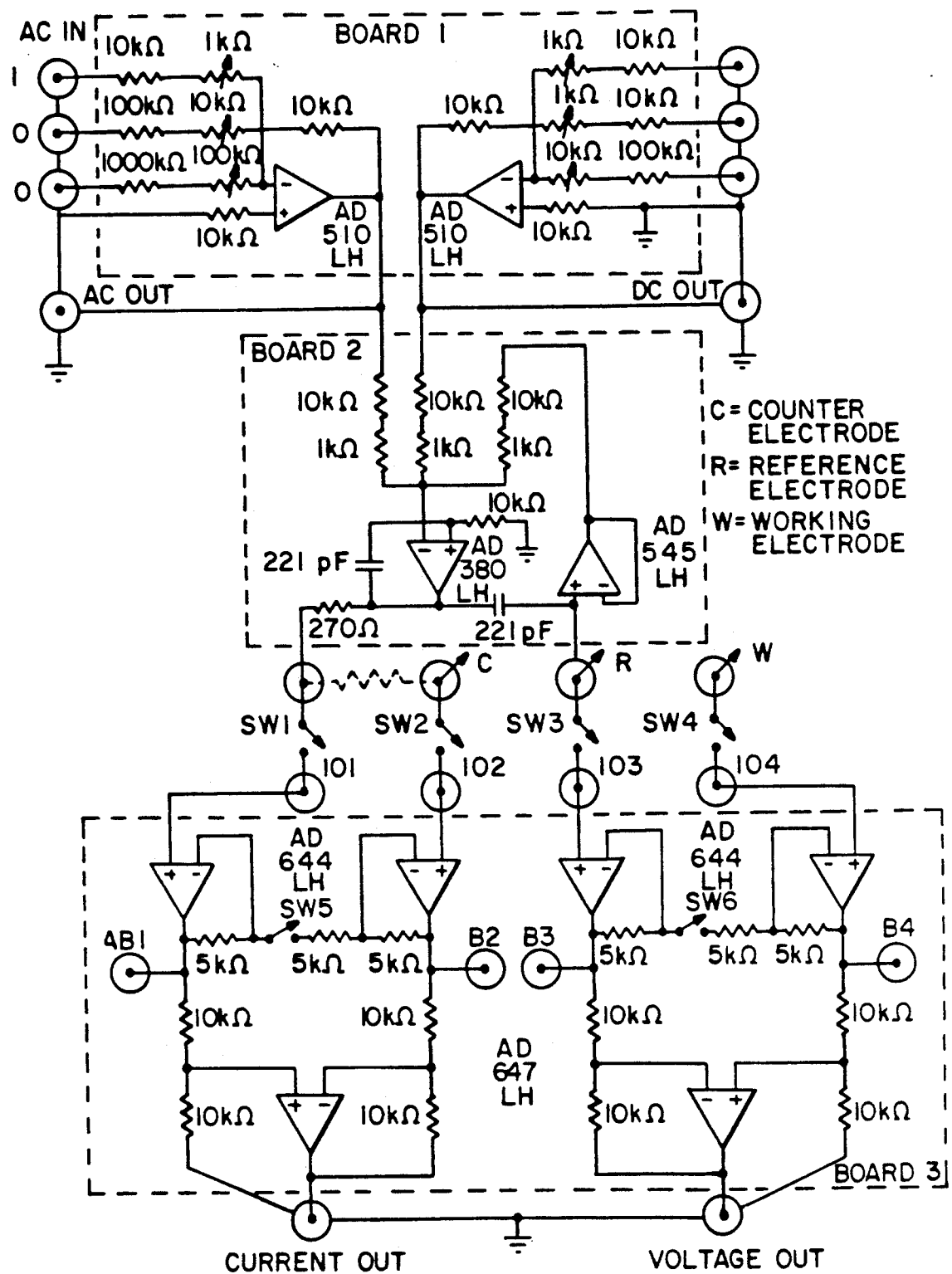
FIG. 2 is a diagram of the potentiostat of FIG. 1 used to impose a potential perturbation with minimal harmonic distortion.

The hardware shown in FIGS. 1 and 2 was developed in order to implement the harmonic method. FIG. 1 shows the automated measuring system developed and used for experimental studies. FIG. 2 shows schematically the high-speed, low-harmonic distortion potentiostat/amplifier system designed and constructed to facilitate harmonic current measurements.

FIGS. 3-8 provide details of the physical geometries of the electrochemical surfaces on which experimental confirmation studies have been performed.

The constants needed are measured using the harmonic response measuring circuit shown in FIG. 1. The frequency response analyzer 10, necessary to measure the harmonic current response to the applied voltage perturbation is, for example, a Solartron model 1250 under the operator control of microcomputer 12. The software controlling the microcomputer 12 is shown in detail in FIGS. 4A and 4B of the incorporated patent application. It is stored on the disc drive 14, with the data resulting from the measurements being stored on drive 16 or 18. The output can also be displayed on a monitor 20. While the computer is interfaced with the cell through the digital DC/AC volt meter 22, the harmonic current readings are made using the high speed, low harmonic distortion potentiostat 24 shown in detail in FIG. 2. A potentiostat of the type shown is designed simply to avoid introducing harmonics other than those created by the corrosion occurring in the electrochemical cell 26. The connections between the potentiostat 24 and both the cell 26 and the frequency response analyzer 10 are schematically indicated in FIG. 1 and on the schematic diagram of the potentiostat (FIG. 2).

The potentiostat 24 is itself a known device which is connected to three electrodes in the solution under study. One electrode W is the metal of interest also known as the working electrode; one electrode R is a reference electrode which has an electrochemical potential fixed with time; and one electrode C is a corrosion resistant counter-electrode that delivers current to the working electrode. The potentiostat 24 measures the potential of the working electrode W with respect to the reference electrode R. If this potential is not equal to the desired (or "set") potential, the current passing between the counter electrode C and working electrode W is automatically adjusted so that the measured and set potentials are made equal.

The potentiostat 24 can be used to change potentials for testing purposes. In this particular analysis, under control of the microcomputer 12, the frequency response analyzer 10 supplies a combined AC (at frequency f) and DC output voltage to the potentiostat 22 via the signal conditioning interface 22. The potentiostat 24 closely maintains the set DC voltage between the working electrode W and the reference electrode R, but supplies the AC with attenuation and phase shift which increase with increasing frequency. The interface unit 22 simultaneously provides the frequency response analyzer 10 with the voltage measured between the working electrode W and the reference R electrodes and the voltage across a resistor in series with the counter electrode C, the latter being proportional to the current.

The harmonic components of the voltages supplied to the frequency response analyzer 5 are measured by a pulse rate multiplication technique. The frequency response analyzer 10 contains a two phase oscillator, operating at a multiple of the frequency supplied to the specimen. The frequency response analyzer 10 digitally computes the product of the unknown voltage and the in-phase quadrature oscillator output voltages with the internal oscillator set to the harmonic of interest. The integral (equivalent of the sum in a discrete point digital device) of these products is computed over an integer number of cycles, normally N = 1, 10, 100, 1000. This accomplishes a digitally demodulated phase-sensitive detection and results in numbers proportional to the magnitudes of the in-phase and quadrature components of the known voltage. The DC and fundamental components of the perturbing voltage (elements 3-5 of the array of FIG. 3 of the incorporated patent application), and the zero to 5th harmonics of the response function (elements 6-16 of the array of FIG. 3 in the incorporated application) are measured sequentially as a function of frequency under control of microcomputer 12. A flow chart of the necessary software is shown in the incorporated application. Measurements are made at logarithmically spaced frequency points between a chosen minimum and maximum frequency. To minimize the transient effects, according to the software as incorporated, all harmonic measurements are made at each frequency before proceeding to the next. Communication over the IEEE standard 488 bus and the microcomputer 12 (for instance, a standard Apple II+ microcomputer) is bi-directional. The Apple II+ supplies AC and DC voltage, frequency, channel, harmonic number, and measurement initiate commands to the analyzer 10.

The analyzer 10 returns real and imaginary components to the microcomputer, 12, at the termination of measurement.

To ensure that the system is operating under kinetic control, and to employ long integration times with tests of relatively short duration, $f_{min}$ is normally set to 10 Hz. At the completion of the measurement cycle, the data is stored in memory 18.

Figure 3:
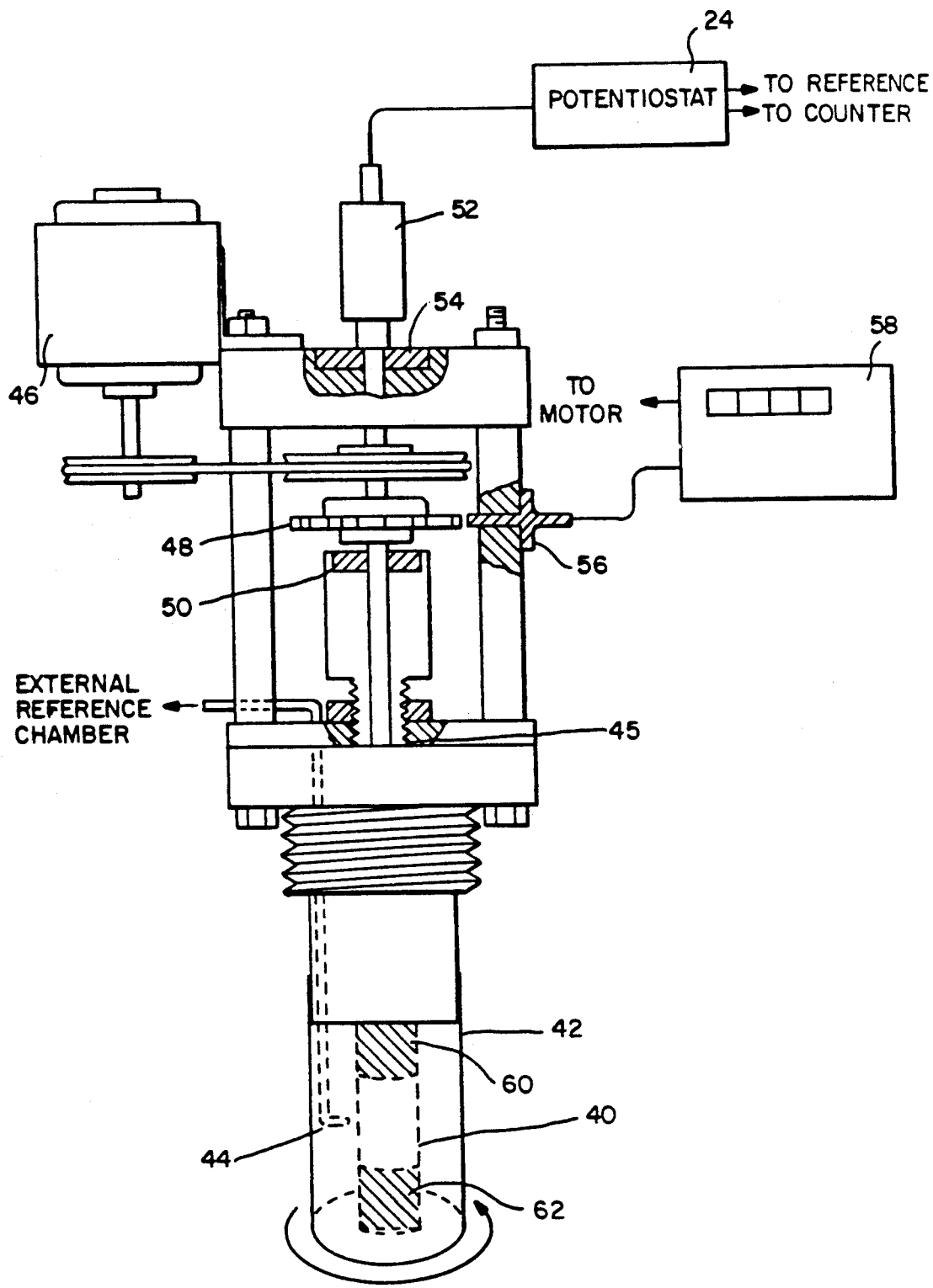
FIG. 3 illustrates a system used to test the measurement accuracy of this invention.
Figure 4:
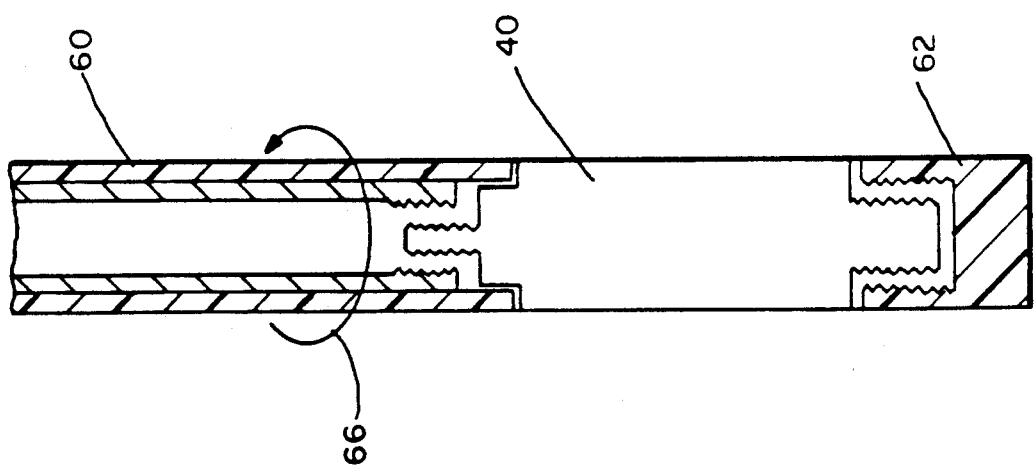
FIG. 4 is a large scale view of the specimen mounting shown in FIG. 3.

FIGS. 3-8 show typical working electrode (specimen) geometries that can be used in conjunction with the harmonic analysis system illustrated in FIGS. 1 and 2. FIGS. 3 and 4 illustrate the simplest case, a rotating cylindrical electrode 40. The counter electrode 42 is a cylinder of titanium surrounding the rotating working electrode 40. Measurements of potentials are made using a Lugin probe 44.

The working electrode 40 is mounted on a shaft 66 which passes through the housing at a seal 45. The housing also supports a motor 46, a gear 48 for indicating the rotation of the electrode 40, and a bearing 50 for supporting the electrode. The potentiostat 24 is shown coupled to the sample through a mercury slip ring 52 rotating on the same shaft as the sample using a bearing mounting 54. A magnetic pickup 56 is used to monitor the rotation of the tooth gear 48 to indicate at 58 the rotational speed of the working electrode 40. It should be noted that the ends of the working electrode 40 shown at 60 and 62 are masked off so that the current flows uniformly from the working electrode 40 to the counter electrode 42 through the annular space, with the potential monitored by the probe 44. This is considered an ideal geometry because by rotating the electrode, the liquid flows across the electrode surface while a current is from the working electrode 40 to the counter electrode 42. This uniform current flow is a condition that maximizes the accuracy of AC impedance measurements.

FIG. 4 is an expanded view of what is illustrated in FIG. 3, showing in greater detail the working electrode 40, the insulators 60 and 62 above and below the working electrode, and the rotating shaft 66 which carries the working electrode in constant rotation.

Figure 5:
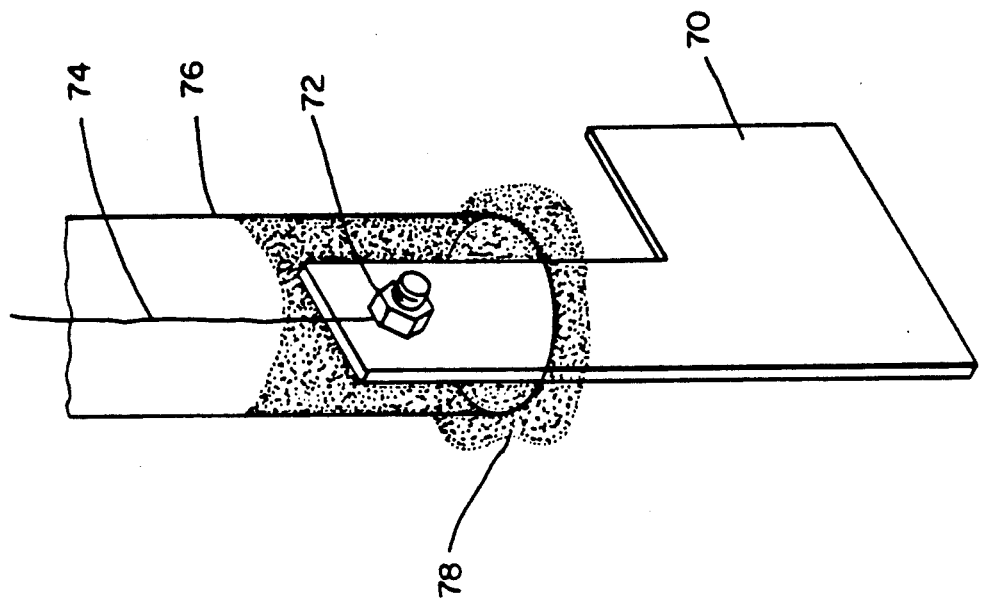
FIG. 5 shows a conventional mass loss measurement specimen.

FIG. 5 is a more conventional specimen of a type typically used for mass loss study comprising a flag-shaped specimen 70, fastened by a nut and bolt 72 to the end of an electrical contact wire 74 which carries current to the mass loss specimen. The specimen is suspended so that the nut and bolt 72 are contained within a thin walled glass tube 76. The specimen is sealed in the tube using silicon rubber indicated at 78. While this electrode is good for studying mass loss in the classical sense, it is more difficult to use with the method proposed, in that the electrode detects current flow more from one side than the other, and does not account for the disturbances of current uniformity which occur at corners of the specimen 70.

Figure 6:
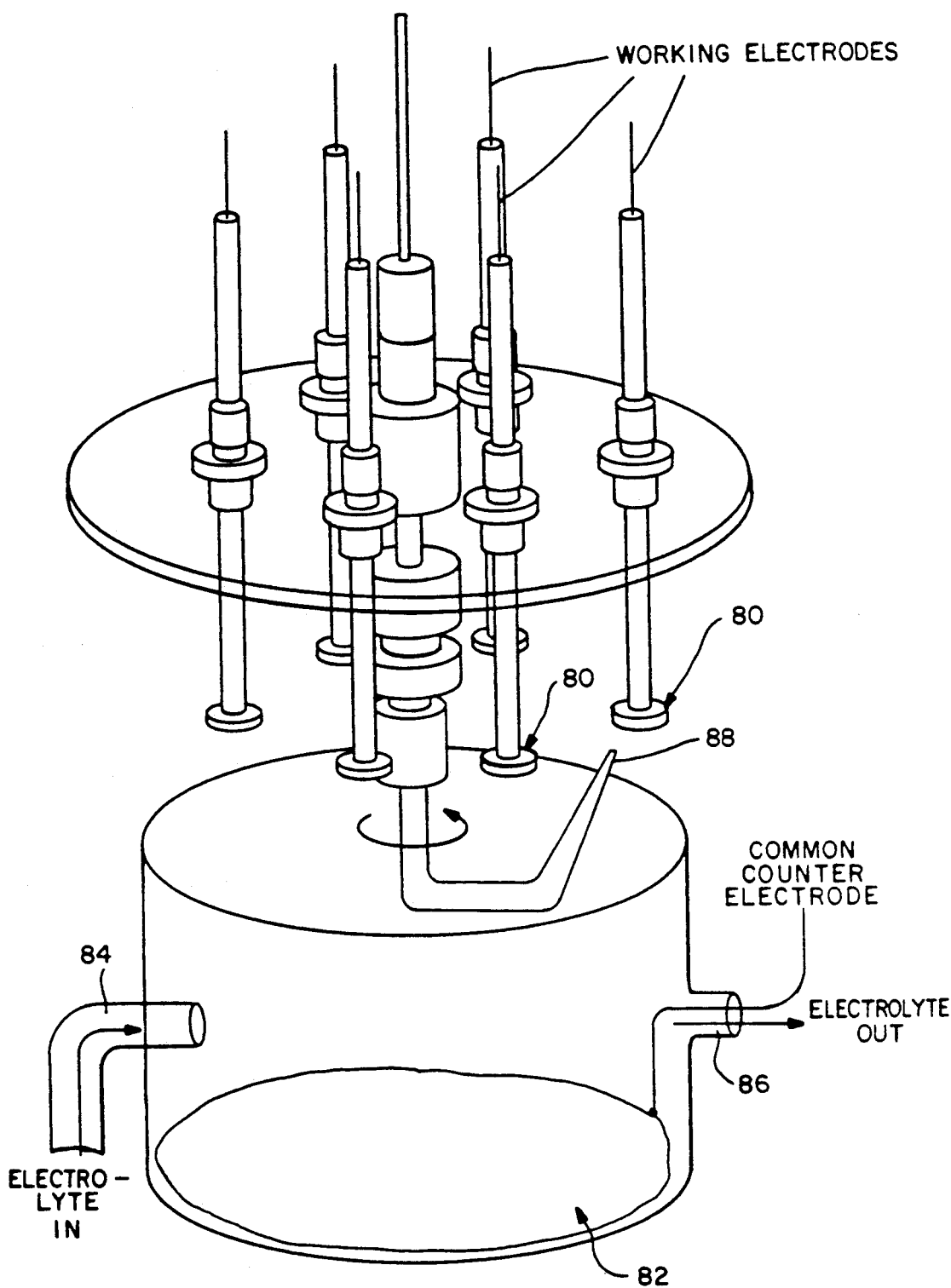
FIG. 6 shows an alternative system to test the measurement accuracy of this invention.

FIG. 6 illustrates a system in which a set of coin-like, or circular flag, working electrodes 80 face a common counter electrode 82 which covers the bottom of the tank through which the corroding electrolyte flows from inlet 84 to an outlet 86. The setup described herein provides a uniform flow of current through the electrolyte to the surface of the circular flag specimen 80 from the counter electrode 82. The electrolyte flows from inlet 84 to outlet 86 at a rate that assures good stirring, effectively reducing diffusion effects.

Figure 7:
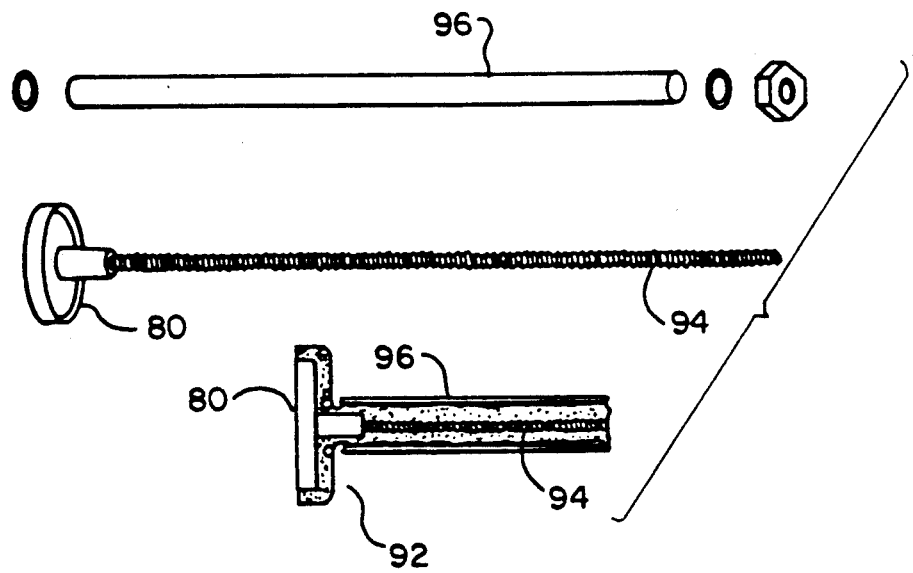
FIG. 7 is a detailed view of the specimen mounting shown in FIG. 6.

FIG. 7 is a detailed diagram, i.e., an exploded view, of the circular flag specimens 80 shown in FIG. 6, surrounded by a masking compound 92 to prevent current flow from surfaces which are not being measured. A threaded conductor 94 is provided which is extended through a glass tube 96 which is used to mount the electrode and to prevent undesired or unmeasured current flow.

Figure 8:
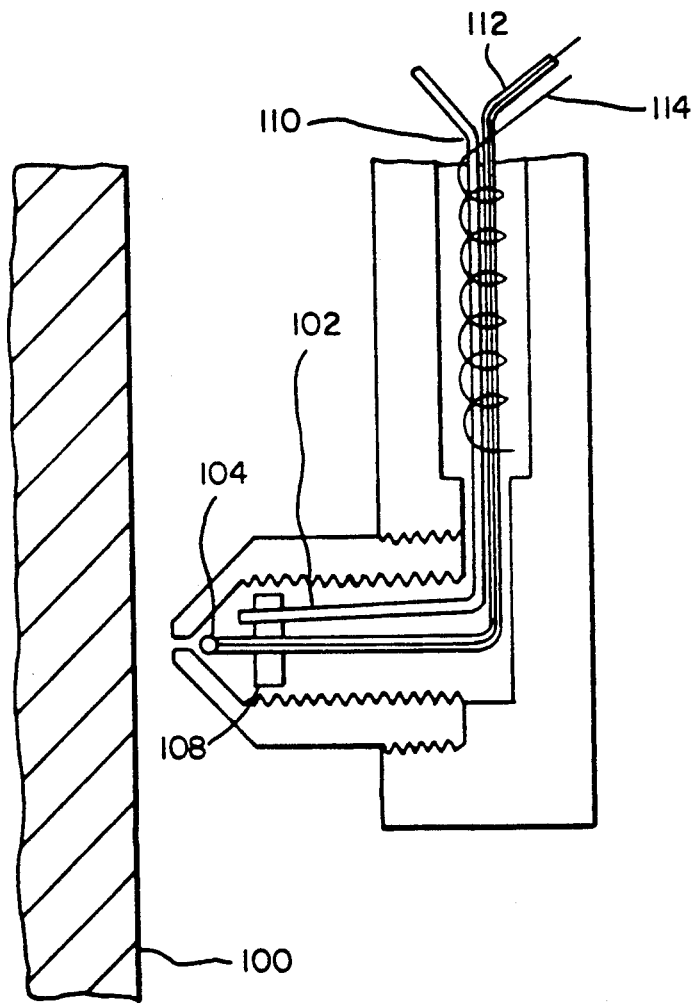
FIG. 8 shows a probe that may be used to measure corrosion rates in a system of practical significance.

FIG. 8 illustrates a probe that could be used to monitor corrosion of a surface 100 in a real system as for example the water box of a power plant condenser. A counter electrode 114 comprising a wire coil is used to impose an AC and/or DC potential perturbation. Potentials are measured with respect to a pseudo-reference electrode 104 or a Lugin probe 102. The separation of these two electrodes is maintained using an insulating spacer 108. An insulating sleeve 112 is used to shield the pseudo-reference electrode contact from the probe electrolyte, and a plastic capillary 110 is used to house the Lugin probe. In this way, these contacts can be brought outside the water box to contact the potentiostat and interface as shown in FIG. 1. A counter electrode 114, comprising a wire coil, is also shown in FIG. 8.

It should be noted that equations 7-18 apply to the free corrosion case, whereas equations 19-21 apply to the situation of applied anodic or cathodic bias, which is the more general case. The difference is the presence of an additional unknown, i.e., the superimposed DC voltage.

A number of experiments have been conducted with the specimens shown above, using seawater. Experimental verification of the validity of the AC harmonic analysis procedure for determining corrosion rates has been obtained for a number of materials in a variety of specimen geometries. Initially, four different specimen geometries were studied: a rotating-cylinder electrode, FIGS. 3 and 4; conventional flag weight loss specimens, FIG. 5; a circular flag specimen multicell, FIGS. 6 and 7; and a surface probe, FIG. 8. The experiments were performed on specimens of 90:10 and 70:30 copper:-nickel alloys, and commercially pure titanium. In addition to AC harmonic analysis measurements at the first, second, third and zero'th (DC Faradaic rectification) harmonics, small-amplitude AC impedance methods were used, DC current/voltage relationships (Tafel plots) were determined, and mass loss data were obtained.

At a later stage, experiments were performed under conditions more closely representative of those likely to be experienced under condenser water box conditions. These experiments were performed using a probe containing reference and counter electrodes that faced a simulated tube/tubesheet structure. This structure was situated inside a flow loop in which natural seawater was pumped such that the velocity in the tubes could be controlled at values as high as 4 m s$^{-1}$.

In all experiments performed, three goals were paramount: demonstration of the harmonic impedance technique as a quantitative indicator of corrosion rates by comparing calculated corrosion rates with the results of mass loss determinations, demonstration of the technique as a qualitative indicator of corrosion by comparing changes in the calculated corrosion rates with those expected from changes in physical variables (cathodic protection potential, flow velocity, aeration, etc.); determination of corrosion mechanisms by examining the effects of physical variables on the free corrosion current and Tafel coefficients. Considerable difficulty exists in comparing the results of the harmonic analysis procedure with those of mass loss when the material is cathodically protected. The materials studied, 90:10 and 70:30 copper:nickel and titanium, corrode very little in seawater, and corrode significantly less under an applied cathodic bias. The precision of mass loss determinations, therefore, was low, because it was very difficult to determine the nature and thickness of the corrosion product film in many instances. Nevertheless, good correlations were achieved between the corrosion rates obtained by the comparisons between mass loss and harmonic analysis methods. Such comparisons were made for rotating cylinder, conventional flag, and circular flag specimens at the free corrosion potential and cathodic bias, and were made for the surface probe and for circular flag specimens under anodic bias. Within the precision and scatter of the mass loss data, satisfactory agreement was obtained between the two techniques.

As a qualitative indication of the utility of the harmonic method, studies were performed to determine the effect of changes in the physical variables (principally applied bias level and seawater velocity) on the calculated corrosion rate. As expected, steady state corrosion rates for all specimen types exhibited a roughly exponential dependence on cathodic overvoltage. For data obtained at a 90:10 copper:nickel tube/90:10 copper:-nickel tubesheet intersection in natural seawater using the surface probe, a plot of log corrosion rate vs. cathodic overvoltage is monotonic and nearly linear for cathodic overvoltages from 0 to 1000 mV.

Figure 9:
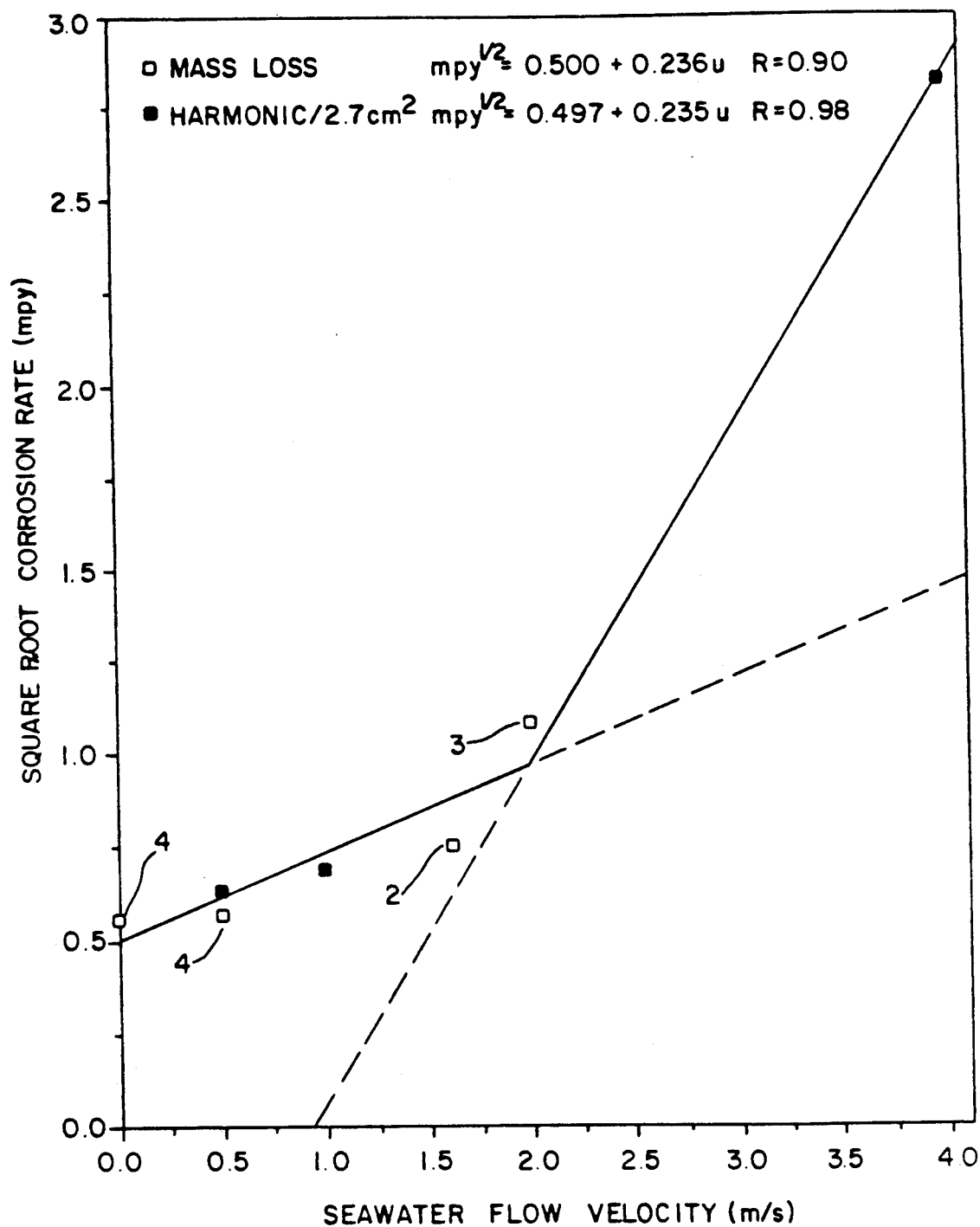

The effect of seawater velocity on the corrosion rate of titanium, copper:nickel alloy, and carbon steel specimens was not observed to be pronounced. For the low flow velocities (up to 63 cm s$^{-1}$) used for harmonic analysis studies of rotating cylinder, conventional flag, and circular flag specimens, no effect of velocity was observed on the corrosion rate. In the range of flow velocities up to 4 m s$^{-1}$ obtained in the flow loop, however, the corrosion rate of a 90:10 copper:nickel tube, measured with the surface probe, exhibited an exponential or parabolic dependence on seawater velocity. FIG. 9 shows the corrosion rates calculated for 90:10 copper:nickel tubes exposed for approximately 34 days by the harmonic analysis method, compared with literature values obtained for long-term exposure. Assuming that 2.7 cm$^2$ is the area of the tube addressed by the surface probe, then there is a remarkable correlation between the two data sets. For data up to 2 m s$^{-1}$, there is an almost exact concordance between the mass loss and harmonic analysis results for 90:10 copper:nickel alloy, with the functional form:

Mass Loss; $mpy^{\frac{1}{2}} = 0.500 + 0.236U$; $R = 0.90$

Harmonic; $mpy^{\frac{1}{2}} = 0.497 + 0.235U$; $R = 0.98$ where U is the flow velocity in m s$^{-1}$ and R is the coefficient of regression.

From an analysis of the variation of the anodic and cathodic Tafel coefficients, it could be deduced that the principal effect of flow velocity was to change the mechanism of the anodic, not the cathodic process, as might have been expected.

The results in FIG. 9 apply at the free corrosion potential. In the cathodic regime, it is very difficult to obtain experimental verification against conventional corrosion rate monitoring techniques, since the rate of corrosion is so low. Instead, partial validation can be achieved by comparing the expected effects of physical variables on the corrosion parameters and rate with the effects measured using the harmonic analysis method. Experiments were performed on all specimen types to determine the effects of absolute time, and time relative to the establishment of a cathodic protection level, on the corrosion rates. To understand the results of these studies, it is necessary to examine the effect of time on the corrosion parameters.

As expected, the application of an applied cathodic bias for 70:30 copper:nickel tubes resulted in a decrease in the measured corrosion rate. An abrupt decrease in the corrosion rate following the application of cathodic protection is associated with a transient change in the electrochemical kinetic processes at the corroding surface. This change in kinetics is evidenced by changes in the free corrosion (exchange) current density and the cathodic Tafel coefficient, suggesting that the mechanism of the cathodic process changes transiently with the application of a cathodic bias. Following the establishment of a cathodic protection potential, however, the values of $\beta_a$ decrease significantly and monotonically with time. These results suggest that, in addition to a transient change in the cathodic process (possibly associated with modification of a surface film), the onset of cathodic protection results in a change in mechanism of the anodic process, resulting in a decrease in the anodic Tafel coefficient for 70:30 copper:nickel tubes. The combined effect of a decrease in the anodic Tafel coefficient and the free corrosion current is an exponential decrease in the corrosion current with time, following the establishment of a steady cathodic protection level.

Validation of the harmonic methods is possible by direct comparison with mass loss results for metal surfaces subjected to an anodic bias. In this case, the rate of metal loss is increased sufficiently to allow precise determination of the mass of metal lost. Confirmatory studies were performed using 90:10 and 70:30 copper:-nickel alloy and 1018 carbon steel specimens. The corrosion rates were measured periodically using the surface probe (FIG. 8) in the flow loop. These instantaneous corrosion currents can be integrated to determine the extent of corrosion; typical results are plotted in FIG. 10. A comparison of the integrated harmonic analysis results for the data shown in FIG. 10 with those of mass loss indicates agreement within 50% for the copper:nickel specimens. This error is probably due to the uncertainty in the metal area monitored by the harmonic probe. The harmonic method underestimated the corrosion rate of the steel specimen by a factor of roughly two. This latter effect is attributable to the presence of a very thick layer of corrosion product which interferes with the corrosion current defected by the harmonic probe.

In summary, the above-described method provides for calculation of the corrosion rate either in the free corrosion condition, or under conditions of applied anodic or cathodic bias.

Modifications of this invention may occur to a person of skill in the art who studies this invention disclosure. Therefore, the scope of this invention is to be limited only by the following claims.

What is claimed:

1. A method for continuous measurement of corrosion rate in a non-coated metal component submerged in an electrolyte comprising the steps of applying a moderate amplitude sinusoidal voltage perturbation having an applied fundamental frequency f to the corroding metal component, and analyzing the harmonic current response arising because of the energy needed to remove an electron from a metal to make an ion at a plurality of frequencies which are multiplies or harmonics of the applied fundamental frequency f to calculate a dissolution current as a representative measure of corrosion, the harmonic current response being a function of said frequency harmonics arising in response to the sinusoidal voltage perturbation with no DC variation of potential.

2. A method as claimed in claim 1 including the further step of measuring the rectification current response to the presence of a small AC voltage perturbation at the frequency f, the dissolution current being calculated based on the harmonic current response and the rectification current response.

3. A method as claimed in claim 2 including the step of calculating the free corrosion current density, the free corrosion potential and the Tafel coefficients, the Tafel coefficients being a measure of the exponential dependence of the rate of corrosion of the material.

4. A method as claimed in claim 3 including the step of calculating the dissolution current based on the Tafel coefficient, and integrating the dissolution current to calculate the mass loss due to corrosion.

5. A method as claimed in claim 1 including the steps of measuring the AC and fundamental frequency components of said sinusoidal voltage perturbation and a plurality of the frequency harmonics of the harmonic current response function sequentially as a function of frequency, calculating the Tafel coefficient as a function of the perturbing voltage and the harmonic current response, and calculating the dissolution current as a function of the Tafel coefficient.

6. A method of monitoring corrosion as claimed in claim 4 wherein said harmonic current response is measured at the free corrosion potential of said metal.

7. A method of monitoring corrosion rates as claimed in claim 4 including the step of applying an anodic bias to the metal during the harmonic current response measuring step.

8. A method as claimed in claim 4 including the further step of measuring the rectification current response to the presence of a small AC voltage perturbation at the frequency f, the dissolution current being calculated based on the harmonic current response and the rectification current response including the step of applying an anodic bias to the metal during the harmonic current response measuring step.

* * * * *